United States Patent [19]

Battista

[11] 4,349,470
[45] * Sep. 14, 1982

[54] PROTEIN POLYMER HYDROGELS

[76] Inventor: Orlando A. Battista, 3725 Fox Hollow Rd., Fort Worth, Tex. 76109

[*] Notice: The portion of the term of this patent subsequent to Apr. 28, 1998, has been disclaimed.

[21] Appl. No.: 246,660

[22] Filed: Mar. 23, 1981

Related U.S. Application Data

[63] Continuation-in-part of Ser. No. 74,014, Sep. 14, 1979, Pat. No. 4,264,493, which is a continuation-in-part of Ser. No. 952,303, Oct. 18, 1978, abandoned.

[51] Int. Cl.$^3$ .......................... C07G 7/00; C08H 1/00; C08H 1/06; C09H 9/00
[52] U.S. Cl. ......................................... 260/117; 3/1.9; 106/125; 106/135; 106/154 R; 106/161; 128/92 C; 260/112 R; 260/123.5; 260/123.7; 264/1.1; 351/160 H; 351/160 R; 351/161; 351/162; 424/177; 424/359; 424/360
[58] Field of Search ............. 260/123.5, 112 R, 123.7, 260/117; 106/161, 135; 264/1.1

[56] References Cited

U.S. PATENT DOCUMENTS

| | | | |
|---|---|---|---|
| 3,099,562 | 7/1963 | Rogers | 260/112 X |
| 3,157,524 | 11/1964 | Artandi | 106/122 |
| 3,393,080 | 7/1968 | Erdi et al. | 260/123.7 X |
| 3,443,261 | 5/1969 | Battista et al. | 260/123.7 UX |
| 3,607,860 | 9/1971 | Yamato et al. | 260/123.5 |
| 3,628,974 | 12/1971 | Battista | 260/123.7 X |
| 3,632,361 | 1/1972 | Battista | 260/123.7 X |
| 3,649,347 | 3/1972 | Battista | 260/123.7 X |
| 3,691,281 | 9/1972 | Battista | 260/123.7 |
| 3,767,437 | 10/1973 | Cruz | 106/161 |
| 3,823,212 | 7/1974 | Chvapil | 260/123.7 X |
| 3,965,063 | 6/1976 | Holcombe | 264/1 X |
| 4,096,870 | 6/1978 | Manfuso | 264/1 X |
| 4,121,885 | 10/1978 | Erickson et al. | 264/1 X |
| 4,123,408 | 10/1978 | Gordon | 264/1 X |
| 4,264,493 | 4/1981 | Battista | 260/112 R |

*Primary Examiner*—Howard E. Schain
*Attorney, Agent, or Firm*—George F. Mueller

[57] ABSTRACT

Protein hydrogel structures formed from natural proteins having an average molecular weight of about 100,000 or less by dissolving the protein in an aqueous acidic solution, crosslinking the protein, and air drying to a moisture content not exceeding 10 percent. The thus dried structure may or may not be bleached with an aqueous solution of an oxidizing agent and thoroughly washed with water. The washed structure is dehydrated by treatment with a water-miscible organic solvent, washed with water, and redried to a moisture content of not more than 10 percent. The structures may be in the form of soft contact lenses, films, fibers, and prosthetics.

25 Claims, No Drawings

PROTEIN POLYMER HYDROGELS

This application is a continuation-in-part of application Ser. No. 74,014 filed Sept. 14, 1979, now U.S. Pat. No. 4,264,493, dated Apr. 28, 1981, which is a continuation-in-part of application Ser. No. 952,303 filed Oct. 18, 1978, now abandoned.

This invention relates to hydrogel forms of natural animal and vegetable proteins which have properties superior to the properties of products prepared in accordance with the method disclosed in the parent application. It more specifically relates to improved compositions and products such as soft contact lenses (disposable, fugitive, and dressing forms), and cosmetic, pharmaceutical, and surgical preparations containing these forms of natural animal and vegetable proteins when used in contact with aqueous liquids. The invention also relates to methods of producing the improved products from such natural proteins.

By natural hydrogel (hydrocolloidal) animal or vegetable protein polymers is meant throughout the specification and claims crosslinked protein polymers of natural origin having an average molecular weight of about 100,000 or less, capable of being swollen by water over a wide range of water contents ranging from as low as 30 percent to 1000 percent and higher based on dry weight while possessing useful rheological control properties for specific end product uses.

This invention provides soft contact lenses capable of being colored completely or at least partly, if desired, using effective protein dyes, lenses that will correct optical defects of the wearer's eye.

This invention also provides contact lenses that may be worn continuously until they become cloudy—and can be thrown away (disposable) and replaced by a fresh lens or a pair of lenses.

The invention also provides a means of controlling the properties of contact lenses—using the same raw materials—so that such lenses may have their properties so engineered in advance that they may be used as corneal dressings, fugitive lenses, or in the form of rigid rheologically-tailored hydrogels, capable of serving as a replacement for vitreous fluids.

This invention further provides a means for controlling the composition and chemistry of the natural protein hydrogels to produce burn and wound dressings having superior properties in the wet state.

A further object of the invention is to adapt this new technology to produce novel fibers for textile and medical uses.

The invention also provides a hydrogel base from which bone-like structures, arteries, and similar prostheses possessing outstanding properties in an aqueous fluid saturated state never before available.

The art has long worked with low molecular weight proteins (such as animal gelatins) and vegetable proteins (such as soybean proteins)—using them with and without varying degrees and types of crosslinking. However, great limitations, especially in wet physical properties of such prior products limited their use, especially in the structural forms described herein. For example, prior art has clearly concluded that gelatin or agar never were found suitable to produce contact lenses (Soft Contact Lens, by Montague Ruben, John Wiley & Sons, p. 25, 1978).

The present invention provides new forms of treated protein polymers that possess unique physical properties, especially in the wet state, properties that are critically dependent upon the specific sequence of controlling pH, the use of a combination of crosslinking agents, and drying the structures to critical levels in accordance with specific stepwise chemical and solvent dehydration sequences. The products prepared in accordance with the present method have increased tensile strengths (about 50 percent greater than those prepared by the method of the prior application), have increased elongations, and have increased gas or oxygen transmission permeability as compared with previously prepared products. The present invention also provides a means for controlling the melting points of the compositions.

In producing my products, it is essential to begin with natural protein raw materials that form clear solutions in water at concentrations up to 30 percent or higher. Ordinary household unflavored gelatin is a typical starting natural animal protein as one starting raw material for this invention and edible soybean protein is a typical starting vegetable protein example.

Depending on the desired end-product form, I have found that controlling such variables as pH, the combination of crosslinking agents, temperature, solids concentration, and solvent dehydration sequences are critical variables. A further critical variable is to air dry at temperatures not exceeding about 35° C. (at atmospheric pressure) to a moisture content in the dried form of not more than 10 percent, preferably 7 percent or less. Drying under vacuum at higher temperatures may be carried out as an alternate drying process. I have found that if these critical steps are not carried out, e.g. if the products are heated to 40° C. or higher at any time prior to the final air drying to not more than 10 percent moisture and do not receive appropriate organic solvent dehydration treatments, unsatisfactory water stability in the final products results. Instead of possessing extremely pliable, bendable, and good physical integrity including superior tear strength properties in the wet state, products that are dried in any manner before initially being air dried to not more than 10 percent moisture, and preferably below 7 percent moisture, in sequence with organic solvent dehydration treatments give products having a cheese texture, extremely brittle and friable physical state when saturated with water. Of course, loss of wet physical integrity such as above described (and clearly characteristic of the prior art) makes the resulting products essentially useless for the products produced by this invention: e.g. soft contact lenses, ophthalmological dressings, artificial corneas, vitreous fluid, novel protein fibers for textile and surgical uses, prostheses such as artificial cartilage and artificial bone, capsules, sutures, burn and wound dressings, etc. The importance of this invention lies in making possible a wide range of products having such a wide line of useful properties from inexpensive and abundant relatively low molecular weight natural protein raw materials.

The products of the present invention are prepared from solutions of the natural protein containing from about 0.5 percent to about 15 percent, by weight, preferably from 0.5 percent to 10 percent, of the protein or mixtures of the proteins. The solution is heated to 60°±5° C. so as to aid in dissolving the protein and produce a clear solution. Following the dissolution of the protein, the pH of the solution is adjusted to about pH 3.5 to about pH 5.5 as by the addition of a suitable acid, such as, for example, hydrochloric or phosphoric acids, to form an aqueous acidic solution of the protein. While maintaining the acidic solution within these temperature and pH ranges, the combination of crosslinking agents is added to and incorporated in the solution with vigorous mixing. The amount of the combination of crosslinking agents added to the solution may vary from about 0.5 percent to about 15 percent, preferably from 0.5 percent to 10 percent, of a combination of at least two crosslinking agents, based upon the weight of the protein.

Preferably, the combination of crosslinking agents includes at least one covalent crosslinking agent although two non-covalent or two covalent crosslinking agents are satisfactory. Typical non-covalent crosslinking agents include ammonium alum, pottasium alum, boric acid, and multivalent metal salts such as aluminum and calcium salts. Covalent crosslinking agents include aldehyde based compounds such as formaldehyde, glyoxal, glutaraldehyde, and the like. Other satisfactory covalent crosslinking agents are non-nitrogen polyfunctional compounds including, for example, epichlorhydrin, dichloropropanol, dichloromethyl and dichlorooctyl ethers, diepoxy-butane, ethylene glycol-dimethacrylate, diethylene glycol-dimethacrylate, and the like. Further satisfactory covalent crosslinking agents are nitrogen containing polyfunctional compounds, including, for example, trichloroisocyanuric acid, hexamethylenediisocyanate, ethylene-bismethacrylamide, tetrachloropyrimidine, dimethlol urea, dimethylol ethylene urea, methylol and dimethylol acrylamide, and the like. One of the crosslinking agents may be used in an amount of at least 0.1 percent, based on the protein, while the balance of the combination of crosslinking agents is comprised of one or more of the agents. A small amount of a peroxidic polymerization initiator, such as ammonium or potassium persulfate, and an activator, such as 2-dimethyleneaminomethyl-acetate or p-tolune sulfonic acid, may be included with the crosslinking agents.

The solution is cast or formed into a desired three dimensional configuration or structure followed by air drying at temperatures not exceeding 35° C. to a moisture content of not more than 10 percent, preferably less than 7 percent. In instances where a clear, water-white product is desired, the dried structure is bleached by the use of an oxidizing agent, such as, for example, hydrogen peroxide, sodium hypochlorite, and the like. Where the characteristic tan color of low molecular weight proteins is not objectionable, this treatment may be omitted. The bleached or unbleached structure is thoroughly washed with water followed by a dehydration treatment by immersion in a water-miscible organic solvent, such as, for example, ethanol, denatured ethanol, isopropanol, acetone, and the like. After the organic solvent treatment, the structure is thoroughly washed with water and air dried at temperatures not exceeding 35° C. to reduce the moisture content to not more than 10 percent, preferably less than 7 percent.

Because the base raw material is proteinaceous, products made in accordance with this invention lend themselves to being permanently dyed in single or multiple colored forms and designs using dyeing procedures commonly applied to polymer materials containing NH, $NH_2$, and COOH groups. Accordingly, any desired color either for functional or cosmetic purposes may be imparted to these products by the addition of suitable dyes or pigments.

The examples which follow are representative illustrations of the invention but are not to be considered as limitations.

EXAMPLE 1

Soft Contact Lenses

A 400 ml clean gel mixture comprising 400 ml of a 10 percent gelatin solution (approximately 90,000 molecular weight and a bloom of about 175) was heated to 60° C. To this clear mixture is added with smooth, steady stirring 4 drops of 10 N HCl bring the pH to 4.30. Immediately thereafter, 10 ml of a 10 percent aqueous solution of ammonium alum, approximately 2.5 percent based on the gelatin, are added with vigorous stirring followed by 4 ml of Formalin, approximately 3.7 percent formaldehyde based on the gelatin. The mixture is stirred vigorously while the temperature is maintained at 60° C.±5° C.

The initial casting of the natural hydrogel, preconditioned as above, to produce a water-stable product must be carried out promptly after the sequential addition of the crosslinking agents. The casting may be done either by stationary air drying in a mold, by spin casting and drying in a mold, or by casting solid films from which hydrogel "buttons" can be punched and subsequently melted in two piece closed molds.

Disposable Soft Contact Lens

From a burette or measuring pipette, 4 drops of the above mixture are carefully added to a special two part polycarbonate mold, preheated to a temperature of 60° C. The thickness of the contact lens—as well as its refractory properties—are predetermined both by the concavity and convexity specifications of the two piece molds, respectively (e.g. male and female counterparts). The hydrogel is allowed to dry slowly at about 25° C. (R.T.) and 90 to 95 percent R.H. for at least 24 hours, during which the crosslinking reaction proceeds essentially to completion.

At the end of this drying cycle, the lenses still in their molds may be given a further drying in an air circulating oven for a minimum of 4 hours at 35°–40° C. maximum to insure that the moisture content at this point of production is reduced to not more than 10 percent, preferably less than 7 percent.

The lenses are easily removed from the molds and immersed in a dilute aqueous solution of household hydrogen peroxide (3 percent by volume) for at least about 1 hour at R.T. (25° C.). This treatment is especially effective in substantially removing the natural tan or light brown coloration characteristic of relatively low molecular weight natural proteins, whether crosslinked or not.

The lenses now receive a vigorous and thorough washing using distilled water, preferably, to insure removal of all residual minute amounts of crosslinking reagent and any residual hydrogen peroxide.

After this thorough washing treatment the water-swollen lenses are added to commercial (either undenatured or denatured) ethyl alcohol (95 percent by volume) and allowed to remain immersed therein for a minimum of two hours.

At the end of the ethyl alcohol dehydration soaking treatment, the lenses are once again washed thoroughly with distilled water to remove all traces of residual ethyl alcohol and related denaturation components if denatured ethyl alcohol is used. Repeated extensive washings in distilled water, preferably, is important at this step. The rehydrated lenses may now be stored in saline solution. Alternatively, the washed lenses may be slowly air dried once again using the precise sequence described above; namely, air dried for 25 hours at R.T. (25° C.) and 90-95 percent R.H., followed by a minimum of 4 hours in an air circulating oven at 40°-50° C. maximum, until the residual moisture content is reduced to not more than 10 percent, preferably below 7 percent. If desired, the water-washed lenses may be dried in their respective molds in which they were originally cast. The dried lenses may be sterilized, if desired, by dry heating at a temperature up to 120° C., or by other methods.

In actual use the lenses are rehydrated and, before inserting into the eye, consist essentially of 10-30 percent by weight of a crosslinked natural protein having a molecular weight of about 100,000 or less, the balance comprising water.

EXAMPLE 2

Viscosity Control Hydrogels

A 400 ml clean gel mixture comprising 400 ml of a 10 percent gelatin solution (approximately 80,000 molecular weight and a bloom of 225) was heated to 60° C. To this clear mixture is added with smooth, steady stirring 4 drops of 10 N HCl, bringing the pH to 4.35. Immediately thereafter, 100 ml of a 5 percent aqueous solution of boric acid, approximately 12.5 percent based on the gelatin, are added with vigorous stirring followed by 2 ml of Formalin, approximately 1.85 percent formaldehyde based on the gelatin. The mixture is stirred vigorously while the temperature is maintained at 60° C.±5° C.

This product is allowed to stand at room temperature (25° C.) for at least 15 minutes with continuous stirring to insure maximum homogenization of the crosslinking process.

The hydrogel is then dried preferably by flash spray drying, thereby converting it into a fine particulate form. Or the hydrogel may be spread out in trays to be slowly air dried.

No matter what drying procedure is used, it is necessary that the moisture content be reduced at the drying step, using maximum temperatures at atmospheric pressure of 30°-35° C., to a residual moisture content of not more than 10 percent, preferably less than 7 percent.

The dry natural protein polymer hydrogel particles are next immersed in a dilute aqueous solution of standard household hydrogen peroxide (3 percent by volume) for at least about 1 hour at R.T. (25° C.). This step is especially effective in substantially removing the natural tan or light brown coloration characteristic of relatively low molecular weight, natural proteins—whether crosslinked or not.

The swollen hydrogel particles now receive a vigorous and thorough washing using distilled water, preferably, to insure removal of all residual minute amounts of crosslinking reagent and any residual hydrogen peroxide.

After the above thorough washing treatment, the water-swollen hydrogel particles are added to commercial (either undenatured or denatured) ethyl alcohol (95 percent by volume) and allowed to remain immersed therein for a minimum of two hours.

At the end of the ethyl alcohol dehydration soaking treatment, the hydrogel particles are once again washed thoroughly with distilled water to remove all traces of residual ethyl alcohol and related denaturation components if denatured ethyl alcohol is used. Repeated extensive washings in distilled water, preferably, is important at this step.

The thoroughly rewashed clear, highly swollen hydrogel clusters are now slowly air dried once again using the precise drying sequence described above—namely, either spray dried or air dried until the residual moisture content does not exceed 10 percent, preferably below 7 percent.

The resulting product is especially suitable when swollen in aqueous solutions containing pharmaceutically or ophthalmologically active agents, such as, for example, pilocarpine hydrochloride solutions for treating glaucoma, for controlling the viscosity and flow properties of the solutions. More importantly, the highly swollen network internal structure of the hydrogel particles provides a means of prolonging the action of included drug components.

EXAMPLE 3

Films, Burns, and Wound Dressings

A 1000 ml clear gel mixture comprising a 10 percent gelatin solution (average mol wt 80,000) is heated to 60° C. To this mixture is added with smooth, steady stirring 10 drops of 10 N HCl, bringing the pH to 4.50. Immediately thereafter, 10 ml of a 10 percent aqueous solution of ammonium alum, about 1 percent based on the gelatin, and 10 ml of Formalin, approximately 3.7 percent formaldehyde based on the protein, are added to the mixture in sequence with vigorous mixing, maintaining the temperature at 60° C.±5° C.

Immediately after thoroughly mixing the above composition, it is deaerated in a vacuum desiccator 29-30 inches of vacuum to help deaerate bubbles. The mixture is next cast into flat Pyrex dishes the dimensions of which are chosen to reflect the final dimensions desired for the film. For example, a circular film or dressing may be made by using a Petri dish, a rectangular film by using a rectangular glass dish. As an alternative procedure, the gel may be spread using a "doctor blade" on a plastic surface.

The hydrogel is allowed to dry slowly at about 25° C. (R.T.) for at least 24 hours, during which the crosslinking reaction proceeds essentially to completion. Depending on the thickness of the film desired, slow air drying may continue for a period of a week or more until all of the hydrogel has been dried to not more than 10 percent moisture, preferably less than 7 percent residual moisture. In order to reduce the drying time, after 24 hours the shaped structure may be further dried in an air circulating oven.

Should it be desired to produce a film which is fabric laminated within or fabric laminated to such hydrogel products, the fine mesh fabric is placed smoothly in the casting chamber before the fluid hydrogel is cast.

Subsequent handling of such cast films follows the sequence of treatments involving bleaching with an oxidizing ($H_2O_2$) agent, if desired, followed by a treatment using organic solvent dehydration steps, etc., all as described for producing contact lenses (Example 1).

EXAMPLE 4

Tubes, Capsules, Arteries, and Other Structural Forms

Using the same formulation described in Example 3, the deaerated hydrogel is poured into a concentric mold in order to cast a tube (or artery), with or without a fabric matrix within the mold.

The crosslinking reaction is allowed to proceed at R.T. (25° C.) and 58 percent R.H. for at least 24 hours and to bring the moisture content to not more than 10 percent. The solid hydrogel is slipped out of its concentric mold to form a tubular structure suitable for use as an artery-like prosthesis.

The tubes are then subjected to bleaching, washing, dehydration, washing, and final air drying steps identical to those described in detail in Example 1.

EXAMPLE 5

Bone-Line Prostheses

The starting raw material for producing both cancellous-like and cortical-like prostheses from the stabilized natural protein polymer hydrogels of this invention is identical to or closely similar to the formulation described in Example 3. One of the major differences involves the use of phosphoric acid in preference to hydrochloric acid to adjust the acidity of the hydrogel prior to the addition of the crosslinking reagent.

The initial water-soluble non-crystalline natural protein solution has intimately dispersed within it calcium phosphate particles or crystals with or without inclusion of other ions such as are found in naturally occurring bone and cartilage. The product consists primarily of an intimate and homogenous physical mixture of the various ingredients and various ions may be included to increase the hardness of the product prior to the addition of the protein crosslinking agents described in prior examples.

The calcium phosphate may be formed by mixing solutions of a soluble calcium salt, such as calcium acetate, and of a soluble phosphate, such as sodium phosphate. In the event other salts and/or ions are to be included, such as the fluoride or carbonate ions, soluble salts, such as calcium fluoride or sodium carbonate, may be incorporated in the salt solutions during the formation of the calcium phosphate. The precise structure of the calcium phosphate compounds formed are complex and the term "calcium phosphate" is used to include dicalcium phosphate, tricalcium phosphate, octacalcium phosphate, hydroxyapatite, carbonateapatite, chlorapatite, fluorapatite, and mixtures thereof.

A modification of Example 3 found to be desirable in producing extremely porous, cancellous-type prostheses is the replacement of water as the protein solvent with a dilute aqueous solution of hydrogen peroxide, for example, a 1 percent by volume aqueous solution. Following dissolution of the protein in the dilute solution of hydrogen peroxide, a sufficient amount of a 25 percent (by weight) aqueous slurry of calcium phosphate was incorporated into the protein solution to provide approximately equal amounts of protein and calcium phosphate. The pH was then adjusted with phosphoric acid and the crosslinking agents added and the mixture vigorously agitated while maintaining the temperature at 60° C.±5° C. The use of the hydrogen peroxide solution as the protein solvent results in the formation of small uniformly dispersed bubbles during the adjustment of the pH and addition of the crosslinking agents and thus forms a uniformly porous structure during crosslinking and drying.

In some instances, it may be preferred to freeze-dry the resulting hydrogel-calcium phosphate compositions in lieu of the usual air drying sequences described in prior examples. In any case, the requisite sequence of drying initially to a moisture content of not more than 10 percent, preferably 7 percent or less, followed by further soaking in hydrogen peroxide (3 percent by volume), organic solvent dehydration, and final drying as described in Example 1, is followed in order to obtain bone-like structures having durable wet-strength properties. For example, when placed in water they exhibit a swelling but remain as coherent structures and do not disintegrate.

These products are new compositions of matter from which useful structures resembling cartilage, bone, and ivory may be produced.

EXAMPLE 6

Fibers, Textile Products, and Sutures

The same composition of water soluble protein hydrogel described for Example 3 is a suitable starting raw material for producing novel fibers capable of being fashioned into many conventional textile forms—webs, fabrics, mats, etc.

The acidified gel (pH 4.50), prior to the addition of the crosslinking agents, is pumped into an antichamber in sequence with a mechanism capable of extruding the hydrogel through spinnerets to form ultrafine fibers or even monofils; such equipment is commonly used in producing viscose rayon and cellulose acetate filaments.

The temperature of the gel is kept at 60° C.±5° C. in the antichamber, prior to being passed through a mixing pump into which the crosslinking agents are metered. The filaments are continuously extruded into long vertical cylindrical drying chambers in which they are dried to a moisture content of not more than 10 percent, preferably 7 percent or less, so that they can be collected on reels or in the form of skeins. Following the initial drying step described above, the filaments are subjected to the same oxidizing treatment (e.g. $H_2O_2$), organic solvent dehydration, extensive final washing, and final drying following the sequence of process steps as described in prior examples.

Such fibers are suitable for a variety of medical and apparel uses. When extruded in the form of small diameter filaments, they may be used as sutures for surgery.

The foregoing examples are representative of the method of this invention and are not to be considered as limitations. For example, in the examples, formaldehyde has been used as the covalent crosslinking agent because of its relatively low cost and ready availability; equivalent amounts of any other covalent agent may be substituted for the formaldehyde. It is apparent that modifications and variations in the constituents and proportions may be made without departing from the spirit and scope of the invention.

What is claimed is:

1. The method of preparing a three-dimensional structure comprising forming an aqueous acidic solution of a non-crystalline, natural animal or vegetable protein polymer or mixtures thereof, the polymers having a low molecular weight not exceeding 100,000, heating the solution to a temperature of about 60° C., adding to and incorporating in the solution at least two crosslinking agents while maintaining the solution at a temperature of about 60° C., drying the solution to a moisture content of not more than 10 percent at a maximum temperature of about 35° C. or equivalent under vacuum to form a crosslinked polymer structure, subjecting the structure to thorough washing with water, subjecting the washed structure to dehydration by immersion in a water-miscible organic solvent, subjecting the structure to thorough washing with water and redrying the dehydrated structure to a moisture content of not more than 10 percent.

2. The method as defined in claim 1 wherein at least one crosslinking agent is a noncovalent crosslinking agent.

3. The method as defined in claim 1 wherein at least two crosslinking agents are noncovalent crosslinking agents.

4. The method as defined in claim 1 wherein at least one crosslinking agent is a covalent crosslinking agent.

5. The method as defined in claim 1 wherein at least two crosslinking agents are covalent crosslinking agents.

6. The method as defined in claim 1 wherein at least one crosslinking agent is a noncovalent crosslinking agent and at least one crosslinking agent is a covalent crosslinking agent.

7. The method as defined in claim 1 wherein the aqueous acidic solution of the protein polymer has a pH of from about 3.5 to about 5.5.

8. The method as defined in claim 1 wherein the protein polymer is an animal protein.

9. The method as defined in claim 1 wherein the protein polymer is gelatin.

10. The method as defined in claim 1 wherein the protein polymer is a vegetable protein.

11. The method as defined in claim 1 wherein the aqueous acidic solution of the protein polymer is an aqueous hydrochloric acid solution of animal protein having a pH of from about 3.5 to about 5.5.

12. The method as defined in claim 1 wherein the aqueous acidic solution of the protein polymer is an aqueous hydrochloric acid solution of gelatin having a pH of from about 3.5 to about 5.5 and the amount of crosslinking agents is from about 0.5 to about 15 percent based on the weight of gelatin.

13. The method as defined in claim 1 wherein the aqueous acidic solution of the protein polymer is an aqueous hydrochloric acid solution of gelatin having a pH of from about 3.5 to about 5.5, the crosslinking agents are ammonium alum and formaldehyde, and the amount of the combination of crosslinking agents is from 0.5 to 15 percent, based on the weight of the gelatin.

14. The method as defined in claim 1 wherein after the aqueous acidic solution of the polymer containing the crosslinking agent is dried to form the crosslinked polymer structure, the structure is immersed in an aqueous solution of an oxidizing agent prior to the initial washing with water.

15. The method as defined in claim 1 wherein the water-miscible organic solvent is ethanol.

16. The method as defined in claim 1 wherein the aqueous acidic solution of the protein polymer is an aqueous hydrochloric acid solution of gelatin having a pH of from about 3.5 to about 5.5, the crosslinking agents are ammonium alum and formaldehyde, the amount of the combination of crosslinking agents added is from 0.5 to 10 percent, based on the weight of the gelatin, after the solution is dried to form the crosslinked polymer structure, the structure is immersed in an aqueous solution of hydrogen peroxide prior to the initial washing with water and the water-miscible organic solvent is ethanol.

17. The method as defined in claim 1 wherein the aqueous acidic solution of the protein polymer is an aqueous hydrochloric acid solution of an animal protein having a pH of from about 3.5 to about 5.5, a slurry of calcium phosphate is incorporated in the acidic solution prior to the addition of the crosslinking agents, the amount of crosslinking agents added is from about 0.5 to about 15 percent, based on the weight of the animal protein and the water-miscible organic solvent is ethanol.

18. A unitary three-dimensional structure having unique wet-strength properties comprising a crosslinked, non-crystalline natural animal or vegetable protein polymer or mixtures thereof, the polymers having a low molecular weight not exceeding 100,000 and formed by the method as defined in claim 1.

19. A unitary three-dimensional structure as defined in claim 18 wherein the polymer is an animal protein.

20. A unitary three-dimensional structure as defined in claim 18 wherein the polymer is gelatin.

21. A unitary three-dimensional structure as defined in claim 18 wherein the polymer is a vegetable protein.

22. A unitary three-dimensional structure as defined in claim 18 which includes calcium phosphate.

23. A unitary three-dimensional structure as defined in claim 18 in the form of a soft contact lens.

24. A unitary three-dimensional structure as defined in claim 18 in the form of a film.

25. A unitary three-dimensional structure as defined in claim 18 in the form of a filament.

* * * * *